US010458910B2

(12) United States Patent
Huang et al.

(10) Patent No.: US 10,458,910 B2
(45) Date of Patent: Oct. 29, 2019

(54) MICRO-LENS IMAGING MULTI-WELL TEST PLATE

(71) Applicant: JINAN UNIVERSITY, Guangdong (CN)

(72) Inventors: Yaoxiong Huang, Guangdong (CN); Jiang He, Guangdong (CN)

(*) Notice: Subject to any disclaimer, the term of this patent is extended or adjusted under 35 U.S.C. 154(b) by 0 days.

(21) Appl. No.: 16/220,020

(22) Filed: Dec. 14, 2018

(65) Prior Publication Data

US 2019/0120758 A1    Apr. 25, 2019

Related U.S. Application Data

(63) Continuation-in-part of application No. PCT/CN2017/076565, filed on Mar. 14, 2017.

(30) Foreign Application Priority Data

May 15, 2016    (CN) .......................... 2016 1 0423773

(51) Int. Cl.
*G01N 21/41*    (2006.01)
*G01N 21/43*    (2006.01)
(Continued)

(52) U.S. Cl.
CPC ..... *G01N 21/4133* (2013.01); *G01N 21/0303* (2013.01); *G01N 21/253* (2013.01);
(Continued)

(58) Field of Classification Search
CPC ........... G02B 13/0055; G01N 21/4133; G01N 21/431; G01N 2201/0639; G01N 21/0303;
(Continued)

(56) References Cited

U.S. PATENT DOCUMENTS

2006/0291239 A1* 12/2006 Hasei .................. G02B 3/0012
    362/600
2007/0053080 A1*  3/2007 Harada ................ G02B 6/0051
    359/809

(Continued)

*Primary Examiner* — Sang H Nguyen
(74) *Attorney, Agent, or Firm* — Prakash Nama; Global IP Services, PLLC

(57) ABSTRACT

Disclosed is a micro-lens imaging multi-well test plate which comprises: a transparent plate of 3-5 mm in thickness with one or more trapezoidal wells locating in the middle of the plate, each of the wells is of an underside of 2-4 mm in diameter, 0.2-0.5 mm in thickness, a trapezoidal dip angle of 60-75°, and has a micro-lens which upper half is hemispherical, lower half is a cylinder, with radius of 0.1~1.0 mm, height of 0.2~2.5 mm, molded on the bottom of the well. The micro-lens imaging multi-well test plate is made of homogeneous optical transparent materials. When the trapezoidal concave wells of the test plate are filled with fluid to immerse the micro-lens, under parallel light illumination, due to the refraction effect of light, the image of micro-lens is a round one with an outer edge that is a black ring. The outer radius R of the black ring is the radius of the micro-lens, the inner radius r of the black ring is a function of the refractive index $n_1$ of the immersion liquid, the refractive index $n_2$ of the micro-lens and the height h of the micro-lens, so the refractive index of the sample fluid can be determined by monitoring the value of the inner radius r of the black ring with known values of R, $n_2$ and h. By using a multi-well test plate for imaging, the individual refractive indices of different sample fluids in all the wells can be determined simultaneously in one measurement.

5 Claims, 3 Drawing Sheets

(51) Int. Cl.
  *G02B 13/00* (2006.01)
  *G01N 21/03* (2006.01)
  *G01N 21/25* (2006.01)

(52) U.S. Cl.
  CPC ....... *G01N 21/431* (2013.01); *G02B 13/0055* (2013.01); *G01N 2021/0307* (2013.01); *G01N 2021/0382* (2013.01); *G01N 2201/0639* (2013.01)

(58) Field of Classification Search
  CPC ......... G01N 21/253; G01N 2021/0307; G01N 2021/0382
  See application file for complete search history.

(56) References Cited

U.S. PATENT DOCUMENTS

| | | | |
|---|---|---|---|
| 2008/0037131 A1* | 2/2008 | Steenblik | B44F 1/10 359/619 |
| 2009/0067055 A1* | 3/2009 | Yamamura | B29D 11/00278 359/622 |
| 2010/0108865 A1* | 5/2010 | Cho | G01N 21/6452 250/216 |
| 2012/0142086 A1* | 6/2012 | Haguet | G01N 21/6456 435/288.7 |
| 2012/0193905 A1* | 8/2012 | Schilling | G02B 3/005 283/74 |
| 2013/0270665 A1* | 10/2013 | Sasaki | H01L 31/02325 257/432 |
| 2015/0123227 A1* | 5/2015 | Ootsuka | G02B 1/11 257/432 |
| 2016/0178965 A1* | 6/2016 | Takayama | G02B 5/08 359/626 |
| 2016/0181309 A1* | 6/2016 | Uehira | H01L 27/14629 257/432 |
| 2017/0242161 A1* | 8/2017 | Zhang | G02B 3/0012 |

* cited by examiner

MICRO-LENS IMAGING MULTI-WELL TEST PLATE

CROSS REFERENCE TO RELATED APPLICATIONS

This application claims priority to China Application Number PCT/CN2017/076565 filed on Mar. 14, 2017.

BACKGROUND OF INVENTION

Technical Field

The claimed invention is related to optical detecting technology, particularly involving a micro-lens imaging multi-well test plate for the detection of fluid refractive index.

Description of Related Art

Known methods exist for refractive index detection, but the current methods have inherent limitations. Such as Abbe refractometer, cannot perform non-disturbance in situ rapid detection on the instantaneous variation of the local or bulk refractive index of a solution. None of the conventional methods is able to determine the individual refractive indices of several different samples in one measurement.

Refractive index is one of the most important physical properties of a solution or a medium which is a function of the solution concentration and temperature. Therefore, by detecting the instantaneous variation of refractive index of a solution, one can obtain information about the composition or concentration change of the solution with time.

The refractive index of a solution also changes with time when there is antigen (Ag) and antibody (Ab) or ligand-receptor reaction in the solution, therefore, by monitoring the variation of refractive index, one can determine if there is antigen-antibody reaction in the solution and the concentration of the antigen or antibody.

The monitor of the refractive index variation in a solution requires methods which can perform non-disturbance in situ rapid detection on the instantaneous value of local or bulk refractive index of the solution, but none of the conventional methods can satisfy the requirements. Furthermore, none of the conventional methods is able to determine the individual refractive indices of several different samples in one measurement. As a consequence, alternate approaches to the technique of fluid refractive index detection are desirable.

BRIEF SUMMARY OF THE INVENTION

According to the presently claimed invention, its object is to provide a micro-lens imaging multi-well test plate which can overcome the limitations of conventional methods and satisfy the requirements of non-disturbance in situ rapid detection on the instantaneous variation of local or bulk refractive index of a solution. In particular, by using the micro-lens imaging multi-well test plate, one can monitor the instantaneous variation of refractive index in a solution with an accuracy of $10^{-6}$, and thereby detect Ag/Ab or ligand/receptor presenting in solution in both qualitative and quantitative manner, while without using any labeling, expensive enzymes, pre-immobilization/modification, and post-washing. The detection is objective, can be performed on very low sample volume (several μL) and finished in 2 minutes. It is of high accuracy, reliability, and its detection limit is as low as pg/mL. It is able to perform multi-path detection on the individual refractive indices of different samples in one measurement.

In order to achieve the above mentioned object, the test plate according to the presently claimed invention is a transparent plate which comprises: a plate of 3-5 mm in thickness with one or more trapezoidal wells locating in the middle of the plate, and each of the wells has a micro-lens molded on the bottom, which upper half is hemispherical, lower half is a cylinder, with radius of 0.1~1.0 mm, and height of 0.2~2.5 mm.

According to another aspect of the invention, the micro-lens imaging multi-well test plate is made of homogeneous optical transparent materials, for example, glassy materials, such as glass; crystalline materials, such as quartz and sapphire; synthetic polymers such as PMMA and polystyrene. It is of transparency ≥90%, mirror finish: Ra 0.01-0.05.

According to still another aspect of the invention, said well in the micro-lens imaging multi-well test plate is trapezoidal well with an underside of 2-4 mm in diameter, 0.2-0.5 mm in thickness, and a trapezoidal dip angle of 60-75°, the trapezoidal shape ensures the liquid surface in the well is a plane surface but not a cambered surface under the effect of additional pressure on liquid surface, so as to have excellent optical imaging quality of the micro-lens.

According to still another aspect of the invention, said micro-lens imaging multi-well test plate is under hydrophilic treatment to avoid molecular adsorption from the molecules of sample especially clinical sample solutions, so as to ensure that the optical imaging quality of micro-lens is not influenced by molecular adsorption.

BRIEF DESCRIPTION OF THE DRAWINGS

For a full understanding of the nature and objects of the present invention, reference should be had to the following detailed description taken in connection with the accompanying drawings in which like numerals in the several drawings are employed to denote like parts, and wherein:

Referring to FIG. 1, FIG. 2 and FIG. 3, there is shown exemplary micro-lens imaging multi-well test plate 101 for measuring refractive index of a fluid sample, which test plate incorporates the principles of the present invention. In a preferred embodiment, when a small drop of sample solution is dropped into the sample well 102 of said micro-lens imaging multi-well test plate 101 to submerse the micro-lens 103, by the illumination of a parallel light, micro-lens 103 forms an image 302 which is a round image with an outer edge that is a black ring owing to the effect of refraction.

The values of r and R in the image of micro-lens 202 is related to the refractive index $n_1$ of the sample fluid, and the refractive index $n_2$ of the micro-lens as described in the following equation:

$$\frac{r}{R} = \sin\alpha - \left(\cos\alpha + \frac{h-R}{R}\right)\frac{\sin\alpha\sqrt{1-k^2\sin^2\alpha} - k\sin\alpha\cos\alpha}{\cos\alpha\sqrt{1-k^2\sin^2\alpha} + k\sin^2\alpha}, \quad (1)$$

where $k=n_1/n_2$, h is the height of the cylindrical part of the micro-lens, $\alpha$ is the incident angle to the spherical surface of the micro-lens.

The refractive index $n_1$ of the sample fluid therefore can be obtained with equ.1 by measuring r and R in the image of micro-lens 302.

Since optical refraction takes place at the speed of light, any instant variation of the refractive index in the solution can immediately induce a change in the radius r of the micro-lens image 302, so by using a high speed camera for imaging, one can monitor instantaneous refractive index change of the sample fluid.

Since the relative refractive index is a function of solution concentration, and dependent on antigen-antibody reaction or other ligand-receptor reactions, so by monitoring the refractive index variation with time in a solution, one can determine the concentration of the solution as a function of time, or determine whether there is antigen-antibody reaction and the amount of antigen in the sample solution by comparing the refractive indices before and after mixing antigen and antibody solutions together.

Figure 1:
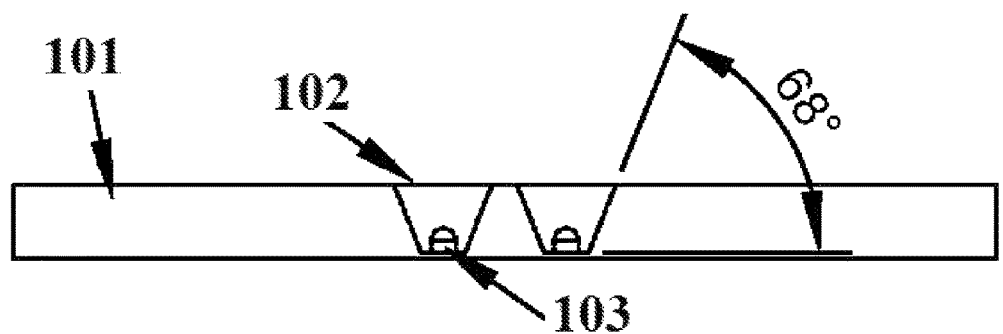
FIG. 1 shows the side view of a 2-path micro-lens imaging multi-well test plate.
Figure 2:
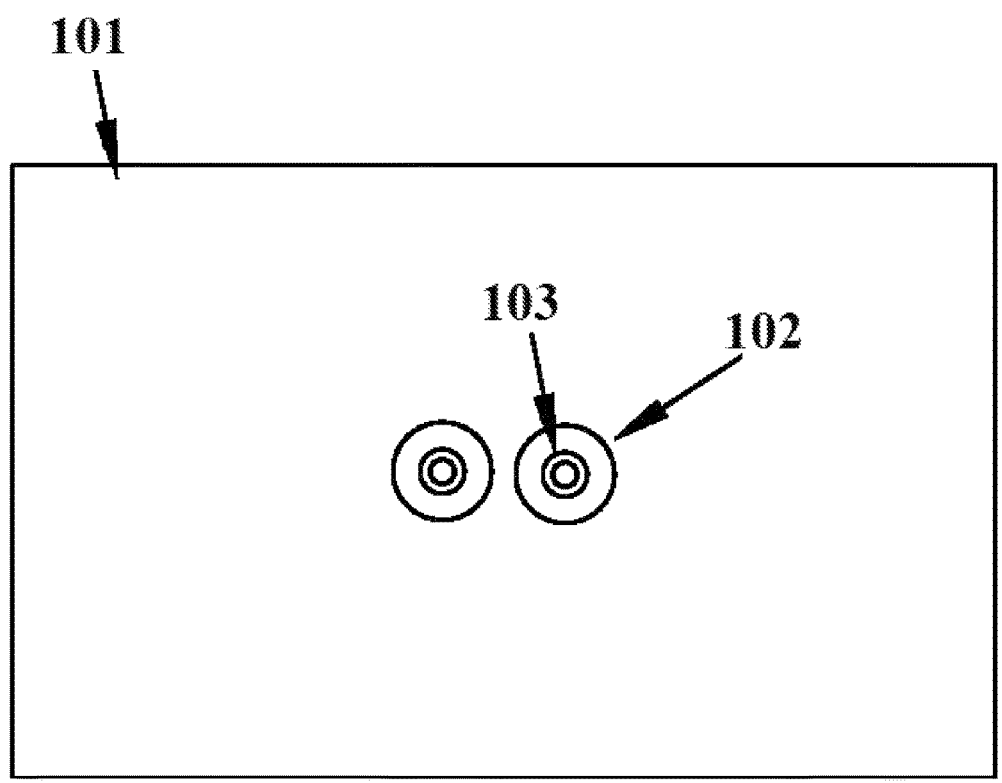
FIG. 2 shows the top view of a 2-path micro-lens imaging multi-well test plate.
Figure 3:
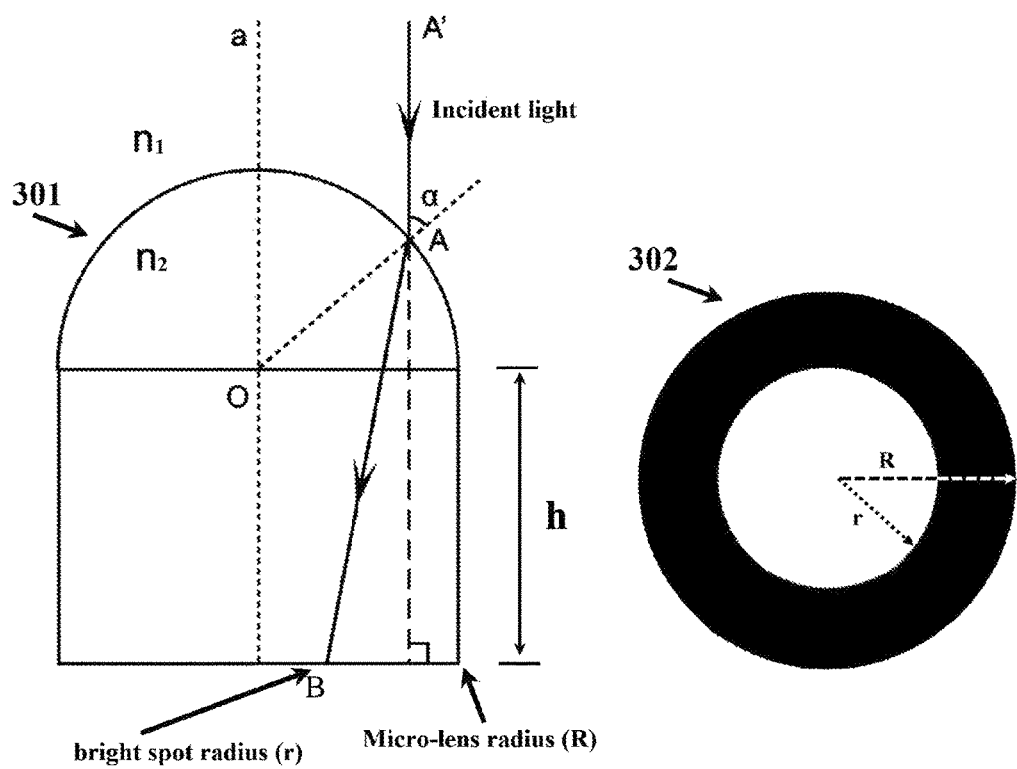
FIG. 3 is the structure of a micro-lens and its image.
Figure 4:
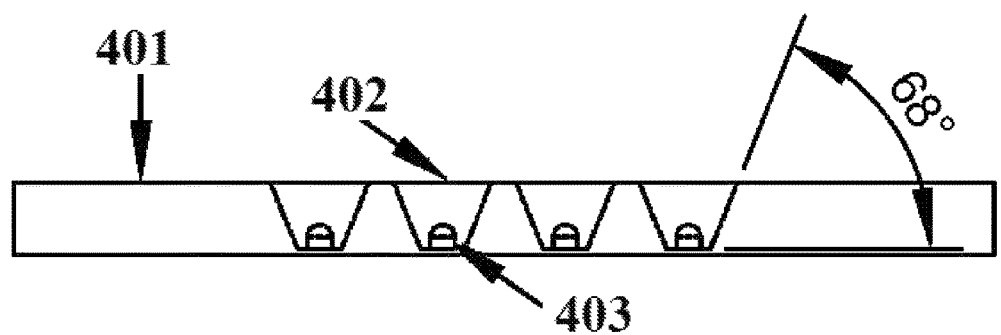
FIG. 4 is the side view of a 16-path micro-lens imaging multi-well test plate.
Figure 5:
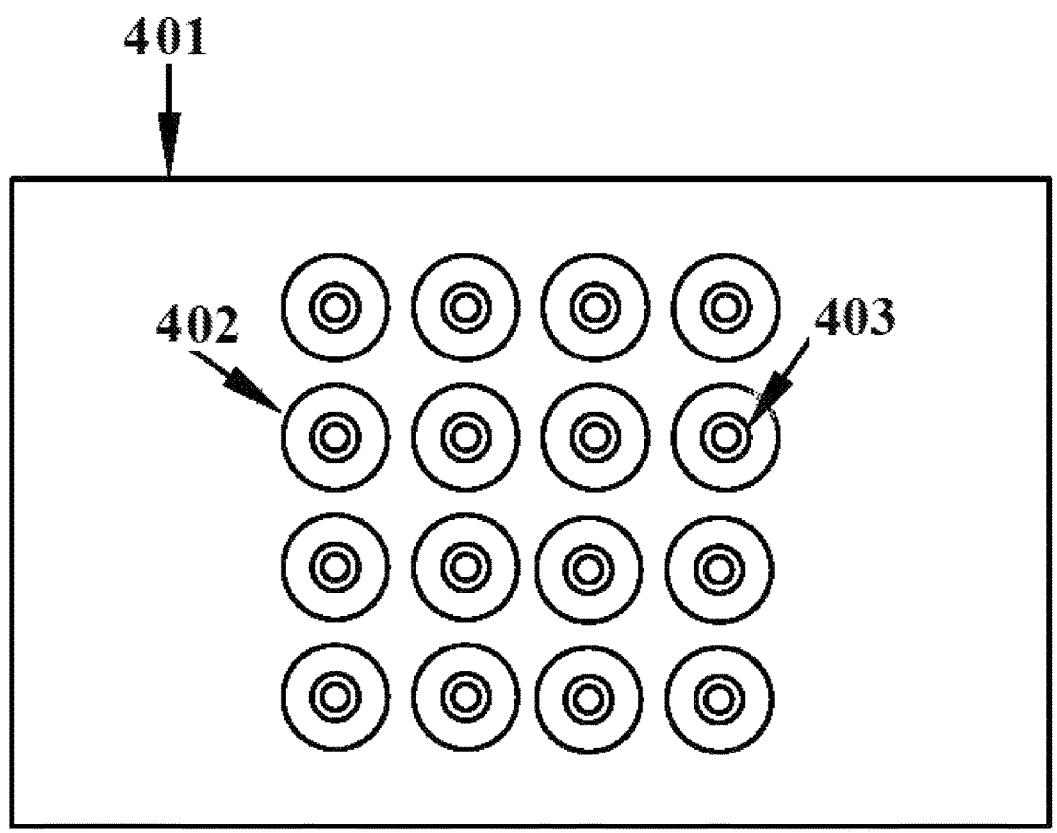
FIG. 5 is the top view of a 16-path micro-lens imaging multi-well test plate.

Referring to FIG. 4 and FIG. 5, by taking the images of all the micro-lenses 403 in said micro-lens imaging multi-well test plate 401 at the same time, one can simultaneously determine the individual refractive indices of the sample solutions in all the wells.

DETAILED DESCRIPTION OF A PREFERRED EMBODIMENT

The following examples and drawings depict an implementation of the presently claimed invention in further detail.

In a First Illustrative Example

The micro-lens imaging 2-path multi-well test plate comprises: a transparent PMMA plate with thickness of 3.5 mm, two trapezoidal wells which underside is 2.5 mm in diameter, 0.25 mm in thickness, and trapezoidal dip angle is 68°; and has a micro-lens with radius of 0.35 mm, height of 1.0 mm molded on the bottom of each well.

The whole micro-lens imaging multi-well test plate is injection molded in one step, its transparency is >90%, mirror finish is Ra 0.025, and under hydrophilic treatment with a hydrophilic treatment reagent DP-9993 (a terpolymer of polyester-polyether-organosilicon) for 24 hours at room temperature.

By dropping some sample fluid into said test well to submerse said micro-lens, and placing said micro-lens imaging multi-well test plate under a phase contrast microscope for imaging, an image of said micro-lens is formed with a high resolution digital camera and the refractive index $n_1$ of the sample fluid is determined by measuring the values of r and R and using equation (1) to an accuracy of $10^{-6}$.

In a Second Illustrative Example

The micro-lens imaging multi-well test plate comprises: a transparent PMMA plate of thickness: 3.75 mm, with 2 trapezoidal wells placing in the middle of the plate which underside is 2.5 mm in diameter, 0.25 mm in thickness, and trapezoidal dip angle is 68°; a glass micro-lens with radius of 0.35 mm, height of 1.0 mm is attached on the bottom of each well.

The glass micro-lens has a transparency of >90%, mirror finish: Ra 0.01, and under hydrophilic treatment with a hydrophilic treatment reagent DP-9993 (a terpolymer of polyester-polyether-organosilicon) for 24 hours at room temperature.

The micro-lens imaging multi-well test plate is injection molded, its transparency is >90%, mirror finish is Ra 0.025, and under hydrophilic treatment with a hydrophilic treatment reagent DP-9993 (a terpolymer of polyester-polyether-organosilicon) for 24 hours at room temperature.

By dropping a small drop of clinical sample solution into said test well to submerse said micro-lens, and placing said micro-lens imaging multi-well test plate on a micro-lens imaging apparatus for imaging, an image of said micro-lens is formed and the refractive index $n_{10}$ of the solution is determined by measuring the values of r and R and using equation (1), then some antibody solution is added into said test well and a similar procedures are carried on to determine the refractive index $n_1$ of the solution after adding antibody solution, by deducing the change between $n_{10}$ and $n_1$, the amount of antigen in the sample solution is determined with an accuracy of 10 pg/mL.

In a Third Illustrative Example

The micro-lens imaging multi-well test plate comprises: a transparent polystyrene plate with thickness of 3.0 mm, and 16 trapezoidal wells which underside is 2.0 mm in diameter, 0.25 mm in thickness, and trapezoidal dip angle is 68°; a micro-lens with radius of 0.3 mm, height of 0.85 mm is molded on the bottom of each well.

The whole micro-lens imaging multi-well test plate is injection molded in one step, its transparency is >90%, mirror finish is Ra 0.05, and under hydrophilic treatment with a hydrophilic treatment reagent DP-9993 (a terpolymer of polyester-polyether-organosilicon) for 24 hours at room temperature.

By dropping some sucrose solutions into said test wells to submerse said micro-lenses in the wells, and performing imaging on all the micro-lenses at the same time with a micro-lens imaging apparatus, the individual sucrose concentrations of different sucrose solutions in the 16 test wells are determined simultaneously.

Since certain changes may be made in the above apparatus without departing from the scope of the invention herein involved, it is intended that all matter contained in the above description or shown in the accompanying drawings shall be interpreted as illustrative and not in a limiting sense. The presently claimed invention may also be applied in a manner not covered by the above-mentioned cases. Other approaches may also be applied which do not deviate from the essence and spirit of the presently claimed invention. Foreseeable changes, modifications, substitutions, combinations or simplifications can be applied as equivalent methods and are included in the presently claimed invention within the scope of protection.

What is claimed is:

1. A micro-lens imaging multi-well test plate that detects a refractive index $n_1$ of at least one kind of fluid, comprising: a transparent plate with a thickness of 3 to 5 millimeters; one or more trapezoidal concave wells locating in the middle of the plate; and a micro-lens having an upper portion being a hemisphere and a lower portion being a cylinder attaching on the bottom of each trapezoidal concave well; said at least one kind of fluid is dropped to each trapezoidal concave well to submerse the respective micro-lens in the fluid in each trapezoidal concave well; said micro-lens is made of homogeneous optical transparent material having a refractive index $n_2$ greater than the refractive index $n_1$ of the fluid immersing the micro-lens, when an incident light illuminates the micro-lens, the micro-lens projects a round image with a black ring at an outer edge of the round image, wherein the black ring has an inner radius and an outer radius; said micro-lens is 0.1-1.0 mm in radius, 0.2-2.5 mm being a height of the cylinder of the micro-lens; with transparency >90%, optical finish; Ra 0.01-0.05; the refractive index $n_1$ is obtained by calculation in which the inner radius of the black ring, the outer radius of the black ring, an angle of the incident light with respective to a spherical surface of the micro-lens, the height of the cylinder of the micro-lens, and a constant k being n1/n2, are variables.

2. The test plate as defined in claim 1, wherein said micro-lens imaging multi-well test plate is made of homogeneous optical transparent materials which comprise glassy materials, crystalline materials and synthetic polymers.

3. The test plate as defined hi claim 1, wherein each trapezoidal concave well is with an underside of 2.5 mm in diameter, 0.25 mm in thickness, and trapezoidal dip angle of 60-75° to ensure that a liquid surface of the fluid dropped in the well is a plane surface under an effect of additional pressure on the liquid surface.

4. The test plate as defined in claim 1, wherein said micro-lens imaging multi-well test plate is under hydrophilic treatment with hydrophilic treatment reagents for avoiding molecular adsorption.

5. The test plate as defined in claim 1, wherein said micro-lens imaging multi-well test plate is of multi-wells and said at least one kind of fluid comprises more than one kind of fluid, so that refractive indices of said more than one kind of fluid are simultaneously detected by taking images of all the micro-lenses in one time.

\* \* \* \* \*